United States Patent [19]

Harder et al.

[11] Patent Number: 4,792,564

[45] Date of Patent: Dec. 20, 1988

[54] METHOD OF TREATMENT AND PREVENTION OF CEREBRAL VASOSPASMS

[75] Inventors: David R. Harder, Hartland; John G. Gross, Elm Grove, both of Wis.

[73] Assignee: The Medical College of Wisconsin, Inc., Milwaukee, Wis.

[21] Appl. No.: 907,772

[22] PCT Filed: Mar. 14, 1986

[86] PCT No.: PCT/US86/00552

§ 371 Date: Aug. 28, 1986

§ 102(e) Date: Aug. 28, 1986

[87] PCT Pub. No.: WO87/05508

PCT Pub. Date: Sep. 24, 1987

[51] Int. Cl.$^4$ .............................................. A61K 31/44
[52] U.S. Cl. .................................................. 514/355
[58] Field of Search .......................................... 514/355

[56] References Cited

U.S. PATENT DOCUMENTS 4,200,640  4/1980  Nagano et al. ..................... 514/355

OTHER PUBLICATIONS

Chemical Abstracts vol. 100; 1984, Columbus, Ohio USA (Sakai et al. 414W).

Chemical Abstracts, vol. 96; 1982, Columbus, Ohio, USA (Aono et al. 28411R).

Primary Examiner—Allen J. Robinson
Attorney, Agent, or Firm—Quarles & Brady

[57] ABSTRACT

A method is disclosed for preventing or treating cerebral vasospasms such as those which usually follow subarachnoid hemorrhage. The method comprises administering to the animal a safe and effective amount of nicorandil to prevent or treat the vasospasm.

4 Claims, No Drawings

METHOD OF TREATMENT AND PREVENTION OF CEREBRAL VASOSPASMS

TECHNICAL FIELD

The present invention relates to a method for the prevention and treatment of cerebral vasospasm, especially the vasospasm which usually follows subarachnoid hemorrhage (SAH).

BACKGROUND ART

Cerebral vasospasms are the leading cause of death and morbidity in cases of subarachnoid hemorrhage. Attempts to define the substance or substances responsible for the cerebral vasospasms which usually follow SAH have not to date been successful.

Many agents including calcium blockers have been used with some success to prevent the formation of such secondary vasospasms. Unfortunately, however, to date, no substances have been available to reverse the cerebral vasospasm once it has occurred. Obviously, the availability of such a product could be a valuable life-saving tool especially where the vasospasms follow SAH caused by trauma.

In the Nagano, et al., U.S. Pat. No. 4,200,640, the compound N-(2-hydroxy ethyl) nicotinamide (nicorandil) is described as being useful in treating circulatory diseases. More specifically, the compound is described as having peripheral vasodilator properties including the properties of a cerebral vasodilator and a renal vasodilator. However, there is no disclosure in the patent that would lead one skilled in the art to believe the compound might be useful for treatment and reversal of cerebral vasospasm.

It is the primary object of the present invention to disclose a method for the treatment of cerebral vasospasms.

It is a further object to disclose a method for preventing the occurrence of cerebral vasospasm.

The method of the present invention comprises administering intravenously to a patient a safe and effective amount of nicorandil to either prevent or to treat the cerebral vasospasm that follows subarachnoid hemorrhage.

The method was discovered using a model that involved the cisternal injection of autologous blood into animals, such as cats and dogs, to produce spasms of basilar and anterior spinal arteries (ASA).

Using this model in cats we found in basilar arteries in spasm significant membrane depolarization resulting from an apparent reduction in K+ conductance ($g_k$). We then set out to determine if there was muscle membrane depolarization in basilar and ASA from dogs using the double injection (of autologous blood) model of SAH and to determine the role of $g_k$ in this regard.

We found that in basilar arteries from double injected dogs 4–7 days post ictus the muscle cell membrane was markedly depolarized. Further electrophysiological analysis suggested that the arterial muscle depolarization resulted from reduction of $g_k$ similar to that found in cat cerebral arteries following SAH.

We then discovered that the use of a drug which specifically increases $g_k$ in a variety of tissues, namely nicorandil (N-(2-hydroxyethyl) nicotinamide), repolarized the arterial muscle cells after exposure to subarachnoid blood. Our data demonstrated that not only does nicorandil repolarize basilar arteries exposed to subarachnoid blood by increasing $g_k$, but that it also reverses the secondary vasospasm in dogs 4–7 days post ictus as evidenced via angiogram and evoked potentials in intact animals. Thus, by using the model to understand the ionic mechanisms of cerebral vasospasm we have been able to develop the method of the present invention which employs a drug which is specific for reversal of that mechanism and reverses the disease state.

MATERIALS AND METHODS

Mongrel dogs 12–18 kg were used. Two days prior to the initial cisternal injection of autologous blood, cortical recording electrodes for evoked potentials were implanted via a small cranial window which was subsequently sealed with the excised bone flap. The dogs were fully anesthetized with 60 mg/kg Na-pentobarbital during the procedure which was done under sterile conditions.

Just prior to the initial injection of arterial blood into the cisternal space, control evoked potentials (somatosensory) and angiograms were obtained. Angiograms were performed by threading a-5 Fr. catheter into the left vertebral artery percutaneously via the right femoral artery. The catheter was placed at the C-3 to C-4 level prior to injection. Catheter placement was confirmed by fluoroscopy. The circulation was visualized via rapid bolus (5 ml) injection of Renografin 60. All x-rays were taken at a constant distance, incidence angle and time after injection of dye. These procedures were done under a constant level of anesthesia via titration of thiopental intravenously. Blood pressure was constantly monitored using a femoral arterial line. After control evoked potentials and angiograms were obtained a cisternal puncture was made using a 20 gauge spinal needle. After removing 3 ml of cerebral spinal fluid, 4 ml of arterial blood was injected into the cisternal space after which the dogs were allowed to recover from anesthesia in our postoperative intensive care unit in the Animal Resource Facility. Two days later the dogs were again anesthetized and another 4 ml of autologous arterial blood (from the femoral artery) was injected cisternally.

From four to seven days post ictus the dogs were again anesthetized for analysis of vasospasm and the effect of nicorandil on the resultant vasospasm following experimental SAH. Evoked potentials and angiograms were obtained before and after intravenous administration of nicorandil for 20 min. The dose of nicorandil used in all 7 dogs studied was between 3-5 ug/kg/min. We found that these low doses of nicroandil had no significant effect on either blood pressure or heart rate, therefore any effect we observed upon administration of the drug could not have been due to autoregulation of cerebral blood flow due to reduction in blood pressure. Arterial blood samples were taken at regular intervals throughout the angiograms and evoked potential experiments and analyzed for $PO_2$, $PCO_2$ and pH via a Radiometer blood gas analyzer.

After obtaining evoked potentials and angiograms before and after drug administration the dogs were sacrificed and the brains removed. The basilar and ASA were removed from the brain for in-vitro analysis of arterial diameter and intracellular electrophysiological recording.

Isolated arterial segments (approximately 1 cm in length) were threaded onto pipettes at either end and tied in placed with 22 um silk suture. All side branches were tied off with similar suture material. One pipette was connected to a pressure reservoir in series with a pressure transducer allowing manipulation of transmural pressure. During eqilibration or addition of nicorandil transmural pressure was set at 100 mmHg maintaining a constant perfusion pressure. Internal diameter of the vessels was monitored via a high resolution binocular microscope (Zeiss) having a trinocular tube connected to a video camera, the image of which was displayed on a video monitor through a VCR and a Colorado Video Image splitter which measured diameter to the nearest micron. In-vitro diameter before and after perfusion of nicorandil was always measured at the mean arterial pressure (transmural pressure) of that particular animal. All arteries in-vitro were suffused and perfused in a muscle myograph with a physiological salt solution containing (in mM): 141 Na+, 4.7 K+, 2.5 $Ca^{2+}$, 0.72 $Mg^{2+}$, 124 Cl−, 1.7 $H_2PO_4^-$, 24 $HCO_3^-$ and 11.0 glucose. Solutions were aerated with 94% $O_2$/6% $CO_2$ $CO_2$ giving a $PCO_2$ of 37–40 torr and pH 7.37–7.4. Temperature was maintained at 37° C. via a water jacket.

Electrophysiological analysis of intracellular events from muscle cells of dog basilar artery was obtained using glass microelectrodes filled with 3M KCl and having tip impedences of 50–80 megohms. Details of electrophysiological analysis have been published previously. When extracellular K+ ($[K]_o$) was changed, extracellular Na+ ($[Na]_o$) was changed in equimolar fashion to keep the sum of $[Na]_o+[K]_o$ constant. Nicorandil ($10^{-9}$ to $10^{-8}$M) was perfused through the vessel by adding the drug to the pressure reservoir to reach the final concentration. This was done, as was diameter measured, at the mean blood pressure of the animal to simulate as closely as possible in-vitro conditions.

RESULTS

A. Electrophysiological analysis of basilar arteries exposed to subarachnoid hemorrhage Intracellular membrane potentials ($E_m$) were measured with glass microelectrodes in isolated, cannulated segments of dog basilar artery which had been exposed to physiological levels of transmural pressure in the muscle myograph. Basilar arteries which had been exposed to subarachnoid blood (4–7 days post ictus) exhibited a resting $E_m$ of $-36.5\pm1.8$ (SE) mV. This compared to a control $E_m$ (not exposed to subarachnoid blood) of $-53.0\pm1.12$ mV. After perfusion of solutions containing $10^{-9}$M nicorandil through the arterial segments for 10–20 min the membrane repolarized to $-51\pm2.1$ mV.

To further characterize the mechanism of the membrane depolarization following SAH we measured $E_m$ as a function of log $[K]_o$. The slope of this line (between 10–100 mM $[K]_o$) is 30 mV/decade. This slope deviates markedly from that observed in control basilar arterial muscle, and from a Nernstian slope of 61 mV/decade for a highly K+ selective membrane. The effect of nicorandil is to increase the slope of the $E_m$ vs. log $[K]_o$ curve in arteries exposed to subarachnoid blood to 47 mV/decade (between 10 and 100 mM $[K]_o$). The slope of the $E_m$ vs. log $[K]_o$ curve is determined by the ratio of permeabilities between Na+ and K+ ($P_{Na}/P_K$ ratio). If this slope was reduced because of a reduced $P_K$ then a drug which acts specifically to increase $P_k$, namely nicorandil, should return the slope toward control; we found this, to be indeed, the case.

Another property observed in arterial muscle upon reduction of $P_K$ and $g_k$ is induction of spontaneous electrical spike activity in previously quiescent cells. We were able to demonstrate the existence of spontaneous spike activity in a depolarized basilar arterial muscle cell exposed to subarachnoid blood. Perfusion of $10^{-9}$M nicorandil in the same artery abolished spontaneous spike activity and hyperpolarized the muscle cell. Under the electrical recordings a histogram was obtained depicting the dilatory action of nicorandil in cannulated basilar arteries exposed to physiological levels of transmural pressure (approximately 100 mmHg). There was a mean increase in internal diameter of hemorrhaged arteries exposed to nicorandil from 336 to 442 microns. Nicorandil had no effect on non-hemorrhaged basilar arteries at this dose.

B. Effect of nicorandil on evoked potentials and angiograms on arteries exposed to SAH From the above data it appears that the membrane depolarization and spontaneous spike activity from arteries exposed to subarachnoid blood is due to reduction of $g_k$ and that such altered ionic conductance is reversed by nicorandil in that its action is to increase $g_k$. If this is the mechanism which occurs in-vivo and is responsible for the vasospasm following SAH, then nicorandil should reverse the vasospasm in the intact animal.

Angiograms taken before SAH (control), 7 days post ictus, and 20 min after intravenous infusion of nicorandil (3 ug/kg/min) showed a partial reversal of the spasm. The data from 5 such experiments showed that on the average, nicorandil, at this very low dose, reduced the secondary spasm following SAH (4–7 days post ictus) by at least 50%. It is conceivable that higher doses would completely reverse the spasm, however, doses beyond 10 ug/kg/min reduce blood pressure which might cause possible autoregulation (dilation) in response to the fall in blood pressure. Blood gases; $PO_2$ and $PCO_2$ remained within normal limits during the duration of the experiments.

One of the most striking effects of nicorandil on the intact animal with experimental SAH was the immediate increase in evoked potential amplitude. The reduction in evoked potential amplitude seen in 6 dogs 4–7 days post ictus and the partial recovery upon infusion of nicorandil (3–5 ug/kg/min) was dramatic. These effects are observed within seconds of initiation of intravenous administration. Such data, suggests an increased functional blood flow resulting from the nicorandil.

In both the prior cat and the above described dog double injection model of cerebral vasospasm following SAH the ionic mechanisms of arterial muscle activation (spasm) involves alteration in resting K+ conductance ($g_k$). Nicorandil has been shown to increase $g_k$ in a variety of muscle types including arterial muscle and is thought to be the primary action of the drug.

Indeed the marked membrane depolarization, reduction in slope of the $E_m$ v. log $[K]_o$ curve and spontaneous electrical spike activity in basilar arteries following SAH strongly suggests reduction in $g_k$; a hypothesis which is greatly strengthened by reversal of these effects with nicorandil.

The angiographic and evoked potential data in the intact animal showing development of secondary vasospasm and marked partial reversal following intravenous infusion of nicorandil demonstrates that the above mechanism is that which occurs in-vivo.

Of interest is the very low dose of nicorandil used in both the in-vitro and in-vivo studies. In the intact animals we used a dose of 3-5 ug/kg/min during intravenous infusion, whereas the doses used previously to lower blood pressure usually exceeded 20 ug/kg/min. At these low doses we observed no changes in blood pressure suggesting that nicorandil acted only on the diseased cerebral arteries in spasm and did not affect overall peripheral vascular resistance. It has been shown that at a suffusion dose of 25 ug/kg/min in dogs there is around a 20 mmHg drop in blood pressure. We have discovered that lower doses have a significant affect on the artery in spasm, but do not reduce blood pressure or cause any possible dilation of cerebral vessels via autoregulation of blood flow. Similarly, perfusion of isolated basilar arteries exposed to subarachnoid blood with $10^{-9}$M nicorandil (a dose significantly lower than its effect on normal non-hemorrhaged arterial muscle) resulted in marked increases in internal diameter. These data suggest that at appropriate dose ranges nicorandil can be specific for cerebral arteries in spasm. It is not known if nicorandil crosses the blood brain barrier under normal conditions, thereby reaching the smooth muscle cells, or if vasospasm increases blood brain barrier permeability.

The nicorandil will normally be administered intravenously or intraarterially in the form of a sterile, parenteral solution. The dose administered should be one which does not lower blood pressure but which does reverse or prevent the vasospasms. The dose will usually range from about 3 to about 10 ug/kg/minute and preferably will be about 3 to about 5 ug/kg/minute. However, the doses may vary upon the size, condition and species of the animal.

It will be readily apparent to those skilled in the art that a number of changes may be made without departing from the spirit and scope of the invention. Therefore, it is intended that the invention not be limited except by the claims which follow.

The embodiments of the invention in which an exclusive property or privilege is claimed are the following:

1. A method of treating cerebral vasospasm which comprises administering to an animal in need thereof by injection into a blood vessel an amount of nicorandil that is safe and effective to treat said cerebral vasospasm.

2. A method of claim 1 in which the nicorandil is administered intravenously.

3. A method of claim 2 in which the amount of the nicorandil administered is about 3 to about 10 ug/kg/minute.

4. A method of treating and reversing the effects of cerebral vasospasm which comprises administering to an animal having such a cerebral vasospasm a safe and effective amount of nicorandil by injection into a blood vessel to reverse the deleterious effects of said cerebral vasospasm.

* * * * *

UNITED STATES PATENT AND TRADEMARK OFFICE
CERTIFICATE OF CORRECTION

PATENT NO. : 4,792,564

DATED : December 20, 1988

INVENTOR(S) : Harder et al.

It is certified that error appears in the above-identified patent and that said Letters Patent is hereby corrected as shown below:

Column 1, lines 3-5, insert the following, as the first paragraph:

--This invention was made with government support under Federal Grants NIH 33833 and 31871 awarded by the National Institutes of Health. The government has certain rights in the invention.--

Signed and Sealed this

Fourth Day of May, 1993

Attest:

MICHAEL K. KIRK

*Attesting Officer*　　　Acting Commissioner of Patents and Trademarks